United States Patent [19]

Willard

[11] 4,061,734

[45] Dec. 6, 1977

[54] METHOD OF THERAPEUTICALLY TREATING WARM BLOODED ANIMALS AND COMPOSITIONS THEREFOR

[75] Inventor: John Wesley Willard, Rapid City, S. Dak.

[73] Assignee: CAW Industries, Inc., Rapid City, S. Dak.

[21] Appl. No.: 733,049

[22] Filed: Oct. 18, 1976

Related U.S. Application Data

[60] Continuation-in-part of Ser. No. 712,158, Aug. 6, 1976, Pat. No. 4,029,770, and Ser. No. 593,712, July 7, 1975, which is a continuation-in-part of Ser. No. 317,097, Dec. 20, 1972, Pat. No. 3,893,943, which is a continuation of Ser. No. 108,198, Jan. 20, 1971, abandoned, said Ser. No. 712,158, is a division of Ser. No. 455,022, March 26, 1974, Pat. No. 3,984,540.

[51] Int. Cl.$^2$ .................... A61K 33/12; A61K 33/06; A61K 35/78
[52] U.S. Cl. ................................. 424/155; 424/127; 424/154; 424/195
[58] Field of Search ................ 424/127, 195, 154, 155

[56] References Cited

PUBLICATIONS

Fiedler et al.–Chem. Abst., vol. 73 (1970), p. 13158q.

*Primary Examiner*—Sam Rosen
*Attorney, Agent, or Firm*—L. S. Van Landingham, Jr.

[57] ABSTRACT

Tissue in warm blooded animals which is damaged and/or infected is treated by administering a therapeutically effective amount of a composition containing a novel catalyst and water soluble catalyst treated lignite. The treatment is also effective in relieving stress and/or shock. In a further variant, warm blooded animals having damaged and/or infected tissue are treated with a composition containing therapeutically effective amounts of at least one antibiotic, the novel catalyst, and the catalyst treated lignite. Novel compositions are provided which contain therapeutic amounts of at least one antibiotic, the catalyst, and the catalyst treated lignite. The novel catalyst and the catalyst treated lignite are prepared by processes described in detail hereinafter.

54 Claims, No Drawings

METHOD OF THERAPEUTICALLY TREATING WARM BLOODED ANIMALS AND COMPOSITIONS THEREFOR

RELATED APPLICATIONS

This application is a continuation-in-part of copending application Ser. No. 712,158, filed Aug. 6, 1976, now U.S. Pat. No. 4,029,770 for a METHOD OF THERAPEUTICALLY TREATING DAMAGED AND/OR INFECTED TISSUE AND RELIEVING STRESS AND/OR SHOCK IN WARM BLOODED ANIMALS AND COMPOSITIONS THEREFOR, and copending application Ser. No. 593,712, filed July 7, 1975 on behalf of John W. Willard, Sr. for A PROCESS FOR TREATING SOLID CARBONACEOUS FOSSIL FUELS AND THE PRODUCTS THUS PREPARED. The aforementioned application Ser. No. 712,158, filed Aug. 6, 1976 is a division of application Ser. No. 455,022, filed Mar. 26, 1974, now U.S. Pat. No. 3,984,540. Application Ser. No. 593,712 is a continuation-in-part of application Ser. No. 317,097, now U.S. Pat. No. 3,893,943, filed Dec. 20, 1972, for NOVEL CATALYST AND PROCESS FOR PREPARING THE SAME. Application Ser. No. 317,097 was a continuation of application Ser. No. 108,198, now abandoned, filed Jan. 20, 1971, for NOVEL CATALYST AND PROCESS FOR PREPARING THE SAME.

BACKGROUND OF THE INVENTION

This invention broady relates to a method of treating warm blooded animals having damaged and/or infected tissue, and/or in a state of stress and/or shock, employing a composition containing therapeutically effective amounts of a novel catalyst and water soluble catalyst treated lignite. In a further variant, the invention relates to the therapeutic treatment of warm blooded animals with an antibiotic in the presence of the catalyst and the catalyst treated lignite. The invention also relates to novel therapeutic compositions which are useful in practicing the method of the invention.

A wide variety of pharmacologically active substances have been prepared heretofore for use in treating diseased and/or damaged tissue in warm blooded animals. However, the pharmacological formulations available heretofore generally have not had a combination of desirable properties including pronounced antibacterial and/or antifungal activity, an ability to promote the curing of infections and/or the rebuilding of damaged tissue, an ability to markedly reduce stress and/or shock, a nonpoisonous nature and capable of being administered as often as desired without harmful effect. Further, entirely satisfactory pharmacological formulations for the open wound-healing of infected and/or damaged tissue including cuts, sores, burns, sprains, bruises, skin irritations and infections have not been available heretofore. A pharmacological formulation capable of acting as a catalyst or synergist when administered in combination with one or more antibiotics also has not been available heretofore.

The present invention provides a composition containing a novel catalyst or synergist and catalyst treated lignite which has the aforementioned desirable properties when used alone in the therapeutic treatment of warm blooded animals. In addition thereto, the composition may be used in the treatment of warm blooded animals in combination with antibiotics to increase the effectiveness thereof by a catalytic or synergistic action. Thus, the composition of the invention has a combination of unusual and unexpected properties which have not been possessed heretofore by pharmalogical formulations in present use.

It is an object of the present invention to provide a novel method of therapeutically treating damaged and/or infected tissue in warm blooded animals.

It is a further object to provide a novel method of relieving stress and/or shock in warm blooded animals.

It is a further object to provide a novel method of markedly increasing the therapeutic effectiveness of an antibiotic administered to a warm blooded animal.

It is a further object to provide novel therapeutic compositions which are useful in practicing the method of the invention.

Still other objects and advantages of the invention will be apparent to those skilled in the art upon reference to the following detailed description and the illustrative specific examples.

DETAILED DESCRIPTION OF THE INVENTION INCLUDING PREFERRED VARIANTS THEREOF

In accordance with one important variant of the present invention, warm blooded animals having damaged and/or infected tissue are therapeutically treated by administering a composition containing therapeutically effective amounts of a novel catalyst or synergist and water soluble catalyst treated lignite. In accordance with a second variant of the invention, warm blooded animals having damaged and/or infected tissue are treated with a synergistic composition containing therapeutically effective amounts of at least one antibiotic, the novel catalyst or synergist, and the catalyst treated lignite. In accordance with a third variant of the invention, synergistic compositions are provided which contain therapeutically effective amounts of at least one antibiotic, the novel catalyst or synergist, and the catalyst treated lignite. Each of these three variants will be described in detail hereinafter. Also, the preparation of the novel catalyst or synergist, which will hereinafter be referred to as a catalyst for the purpose of simplifying the discussion, and the preparation of the catalyst treated lignite will be described more fully hereinafter.

In practicing the aforementioned first variant of the invention, the composition may be administered by topical application of a liquid suspension or solution of the catalyst and catalyst treated lignite or in dry form, or by parenteral injection of a liquid suspension or solution of the catalyst and catalyst treated lignite, or orally in liquid or in solid form. Preferably, the catalyst is in the form of an aqueous suspension and the catalyst treated lignite is water soluble as the resultant composition may be easily administered by topical application to the infected or damaged area, or by parenteral injection, or orally such as in drinking water or food. The catalyst need be administered only in a catalytic amount and the catalyst treated lignite in a therapeutically effective amount. For example, about 0.0000001-0.5% by weight and preferably about 0.00001-0.1% by weight or less of the catalyst, and about 0.000001-1% by weight and preferably about 0.00001-0.5% by weight or less of the catalyst treated lignite may be administered orally or by parenteral injection based upon body weight. In instances where the composition is applied topically, then it may contain, for example, about 0.0000001-1% by weight and preferably about 0.000001-0.5% by weight of the catalyst or less, and about 0.000001-2% by weight and preferably about 0.00001-1% by weight or less of the catalyst treated lignite. While aqueous suspensions or solutions of the catalyst and catalyst treated lignite are usually preferred, other liquid pharmaceutically acceptable carriers may be used. Additionally, the dry composition may be administered in some instance with good results such as when in the form of powder, tablets or capsules. The catalyst and catalyst treated lignite are harmless in reasonable amounts and usually the composition may be administered as often as is needed without harmful effect. However, as a general rule one to three applications or doses per day are adequate and additional applications or doses per day are not beneficial.

The aqueous composition is especially effective in open wound-healing and in treating cuts, open sores, burns, sprains, bruises, foot rot, pink eye, splints, saddle gall, skin irritations and infections, and the like in domestic animals such as dogs, cats, cattle, sheep, horses and poultry. The presence of a therapeutically effective amount of the composition promotes the rate of healing of damaged tissue very markedly and there is a much faster recovery. The aqueous composition also exhibits very powerful antibacterial and antifungal properties and thus it is useful in fighting infections in general of the types commonly contracted by domestic animals. In addition thereto, the composition has a pronounced soothing effect and it is capable of relieving stress and/or shock. The composition alone may be used for this purpose in instances where controlling stress and/or shock is an important factor in the successful treatment of a warm blooded animal.

In instances where the aqueous composition is applied topically, then often it is preferred that an ultraviolet light absorber be added. An example of one presently preferred ultraviolet absorber is Gentian Violet. Following topical application of the composition, the ultraviolet light absorber is thought to absorb ultraviolet light at the site of the damaged or infected tissue and to thereby aid in promoting the rapid repair and healing thereof, and/or to control infections. The composition is very effective in preventing, controlling or therapeutically treating infections of the digestive tract of domestic animals such as intestinal influenza and the like, respiratory infections in general such as pneumonia, and diseases commonly contacted by poultry. It is usually preferred that the composition be administered daily in drinking water and/or in feed and especially when preventing or controlling infections. Parenteral injection may also be useful in some instances.

In accordance with the aforementioned second variant of the invention, one or more antibiotics may be administered to a warm blooded animal in combination with a therapeutic amount of the composition. The specific antibiotic to be administered in a given instance, the amount, and the method of administering the same may be in accordance with prior art practice. However, usually much smaller quantities of the antibiotic are needed to produce comparable results. Often only one-fourth to one-half as much of the antibiotic as is normally required need be administered and sometimes even less.

The composition may be administered alone, with the antibiotic, or separately therefrom. The methods of administering the syneagis combination of the antibiotic and the composition may be as given hereinbefore for the composition alone. The quantity of the composition to be administered also may be as aforementioned, but it is understood that the dosage may vary widely in view of the catalyst and catalyst treated lignite being harmless and the fact that only a catalytic amount of the catalyst and a therapeutic amount of the catalyst treated lignite need be present.

Surprisingly, the synergistic combination of the antibiotic and the composition often is useful in treating infections where the antibiotic alone or the composition alone is of little therapeutic value. For example, the synergistic combination of the antibiotic and composition is highly effective in treating cancer eye in cattle and foot rot in cattle and sheep whereas treatment with either component alone will not result in a permanent cure.

The synergistic combination of the antibiotic and the composition may be used in treating all of the diseases treated heretofore with antibiotics alone. Examples of antibiotics which may be used in practicing the invention are as follows:

amicetin,
aureomycin,
aureotracin,
bactitracin,
bleomycin,
carbomycin,
coumermycin,
cephalasporins,
chalcomycin,
chlorotetracycline,
chromomycin,
condicidin,
cycloserine,
endomycin,
erythromycin,
furacin,
gentamicin,
grisonomycin,
halomicin,
libanomycin,
lincomycin,
melanomycin,
methicillin,
mitomalcin,
moenomycin,
novobiocin,
meomycin,
oligomycin,
pactamycin,
penicillin,
polymycin,
protomycin,
spiramycin,
streptomycin,
streptothicin,
telomycin,
tetracycline,
tetramycin,
thioaurin,
zygomycin.

The preparation of antibiotics such as those aforementioned and/or the use thereof in the treatment of infections in warm blooded animals is disclosed in numerous publications, including the following U.S. Pat. Nos.:

2,442,006;
2,443,962;
2,572,897;
2,602,041;
2,633,445;
2,743,268;
2,746,902;
2,749,273;
2,751,324;
2,795,528;
2,909,464;
2,927,057;
2,943,024;
2,943,025;
2,963,403;
2,990,330;
2,992,162;
3,008,875;
3,023,105;
3,023,145;
3,061,516;
3,065,137;
3,067,100;
3,089,827;
3,147,184;
3,155,587;
3,205,137;
3,279,923;
3,304,231;
3,313,691;
3,323,998;
3,350,267;
3,351,582;
3,359,164;
3,501,570;
3,510,555;
3,511,909;
3,644,617;
3,665,003;
3,681,491;
3,696,194;
3,708,477;
3,708,480;
3,772,438.

The teachings of the above United States patents are incorporated herein by reference.

The present invention also provides novel therapeutic compositions containing a synergistic combination of one or more antibiotics, the catalyst and the catalyst treated lignite. A pharmaceutically acceptable carrier may be present when desired. Such synergistic compositions may be administered to a warm blooded animal in accordance with prior art practice for the antibiotic alone and the treatment may be continued until the infection is cleared up and/or the tissue is healed.

The reasons for the unusual and unexpected therapeutic properties of the composition when used alone are not fully understood at the present time. However, it is thought that the composition promotes or synergizes benefical reactions between the infected and/or damaged tissue and body fluids, air and/or water or components thereof in contact with tissue, and thereby provides an environment which is beneficial in controlling infections in infected tissue and/or promoting the healing of damaged tissue. When the composition is used in combination with an antibiotic, in addition to the foregoing, it also acts as a synergist and increases the effectiveness of a given dose of the antibiotic, and allows less antibiotic to be used for a given degree of effectiveness. In a number of instances, the resultant synergistic combination is capable of providing a cure for diseases such as cancer eye for the first time.

The preparation of the novel catalyst or synergist of the invention is described below, and the preparation of the catalyst treated lignite is described thereafter. In instances where an aqueous suspension or solution of the catalyst and catalyst treated lignite is used in the method of the invention, then the concentrations of the catalyst and/or catalyst treated lignite often may be as set out hereinafter.

PREPARATION OF THE CATALYST

The catalyst used in practicing the present invention may be prepared as described below. In the presently preferred process for preparing an aqueous suspension of the catalyst, a water soluble alkali metal silicate is admixed and reacted with an aqueous solution of a water soluble dissolved substance which is a source of calcium ion and a water soluble dissolved substance which is a source of magnesium ion to produce a finely divided or colloidal suspension of the reaction product. The aqueous solution contains the dissolved substances initially in amounts to provide between about $1 \times 10^{-4}$ and $1 \times 10^{-1}$ mole per liter each of calcium ion and magnesium ion, preferably between about $1 \times 10^{-3}$ and $1\ 33\ 10^{-2}$ mole per liter, and for still better results between $1 \times 10^{-3}$ and $6 \times 10^{-3}$ mole per liter. The dissolved substances should also be present in amounts to provide a molar ratio of calcium ion to magnesium ion between about 2.0:1.0 and 1.0:2.0, and preferably about 1.5:1.0 and 1.0:1.5. For best results, the aqueous medium should contain the dissolved substances in amounts to provide between about $2.5 \times 10^{-3}$ and $3.0 \times 10^{-3}$ mole per liter each of calcium ion and magnesium ion, and the molar ratio of calcium ion to magnesium ion should be about 1.0:1.0, e.g., $2.9 \times 10^{-3}$ mole per liter of calcium ion and $2.7 \times 10^{-3}$ mole per liter of magnesium ion. The alkali metal silicate should have an alkali metal oxide to silicon dioxide ratio between about 0.9:1.0 and less than 2.0:1.0, and preferably between about 0.9:1.0 and 1.2 1.0. The alkali metal silicate should be admixed with the aqueous medium in an amount of about 0.05-2 moles per liter, preferably about 0.1-1 mole per liter, and for still better results about 0.2-0.5 mole per liter. For best results, the alkali metal silicate should be an alkali metal meta-silicate having an alkali metal oxide to silicon dioxide ratio of about 1:1, and it should be admixed with the aqueous medium in an amount to provide about 0.2-0.3 mole per liter, e.g., about 0.25 mole per liter.

Examples of sources of calcium ion and magnesium ion for use in preparing the aqueous solution include mineral acid salts such as the halides, sulfates, bisulfates, nitrites, and nitrates of calcium and magnesium. The chlorides are usually the preferred halides, and both calcium and magnesium chloride are soluble and may be used. Magnesium sulfate and bisulfate are soluble and often are the preferred sources of magnesium ion. Calcium sulfate is only slightly soluble in water and usually is not a preferred source of calcium ion, but calcium bisulfate is somewhat more soluble. While calcium and magnesium nitrite or nitrate are soluble in water and may be used, these substances are not preferred in most instances. The sources of calcium ion and magnesium ion are dissolved in the aqueous medium in amounts to provide calcium ion and magnesium ion within the above ranges. Complete ionization is assumed when calculating the quantities to be dissolved and any desired order of addition is satisfactory. For example, the source of calcium ion may be added to the aqueous medium before, during or after the source of magnesium ion.

The alkali metal silicate to be admixed with the aqueous medium is preferably a water soluble sodium or potassium silicate having an alkali metal oxide ($M_2O$) to silicon dioxide ($SiO_2$) mole ratio between about 0.9:1.0 and less than 2.0:1.0, and preferably between about 0.9:1.0 and 1.2:1.0. The best results are usually obtained with an alkali metal metasilicate having an alkali metal oxide to silicon dioxide ratio of about 1:1. Hydrated alkali metal silicates dissolve faster and should be used for best results when the alkali metal silicate is added in solid form. In instances where an anhydrous alkali metal silicate is used, it may be desirable to dissolve it in water and then add the solution to the aqueous medium. Sodium metasilicate is preferred and usually a hydrated sodium metasilicate such as the pentahydrate gives the best results.

Carbonate ion and/or bicarbonate ion should not be present in the aqueous medium in substantial concentrations as the calcium ion and magnesium ion are precipitated in the form of their respective carbonates. The free carbonate ion and/or bicarbonate ion concentrations in the aqueous medium should not exceed about 10 parts per million by weight based upon the combined weight of the water and the ingredients added thereto and for this reason, the alkali metal silicates should be substantially free of carbonate ion and bicarbonate ion. A small amount of precipitated calcium carbonate and/or magnesium carbonate may be present in the aqueous medium provided additional calcium ion and magnesium ion are available to meet the above defined concentrations.

Distilled water and/or deionized water are usually preferred over a natural or untreated water when preparing the aqueous medium. In instances where water is used which contains substantial initial concentrations of alkaline earth metal ions, then this should be taken into consideration in calculating the amounts of the sources of calcium ion and magnesium ion which are necessary to arrive at the final concentrations previously discussed.

An electrolyte which aids in the preparation of colloidal suspensions may be present in the aqueous medium at the time of admixing the alkali metal silicate therewith. Examples of electrolytes include those used in preparing prior art colloidal suspensions such as the alkali metal halides, sulfates and bisulfates. Sodium chloride, sodium sulfate and sodium bisulfate are usually preferred. The electrolyte should be added in small amounts such as, for example, about 0.00001-0.1 mole per liter, but often larger or smaller amounts may be present.

The conditions under which the alkali metal silicate is admixed with the aqueous medium and reacted with the sources of calcium ion and magnesium ion are not critical provided the reaction mixture is maintained in the liquid phase. The reaction temperature may be, for example, between the freezing point and boiling point of water under the existing pressure conditions. At atmospheric pressure, the temperature is usually about 10°-90° C and often a more convenient temperature is about 20°-50° C. In many instances, ambient or normal room temperature is satisfactory.

The degree of agitation is not critical, and mild to vigorous agitation may be employed during addition of the alkali metal silicate. For the best results, the aqueous medium should be agitated sufficiently to assure rapid and uniform admixing of the alkali metal silicate. After completing the addition of the alkali metal silicate, when desired the agitation may be continued for a sufficient period of time to assure complete reaction and aging of the resulting colloidal suspension, such as for approximately 1-5 minutes to 1 hour or longer.

Upon admixing the alkali metal silicate with the aqueous medium, it takes on a turbid appearance but in most instances no significant amount of visible precipitate is formed. The colloidal suspension of the reaction product thus produced should be strongly basic and may have a pH value of, for example, approximately 10-14 and preferably about 11-13, and for best results about 12. In view of this, the initial pH value of the aqueous medium containing the dissolved sources of calcium ion and magnesium ion is of importance and should be about 6-9 and preferably about 7-8. When necessary, it is possible to adjust the pH value of the aqueous medium to the foregoing levels either before during or after addition of the alkali metal silicate by adding bases such as sodium or potassium hydroxide, or mineral acids such as sulfuric or hydrochloric acid.

The colloidal suspension may be stored for several weeks or longer while awaiting the further treatment described hereinafter. In instances where the colloidal suspension is to be stored over a substantial period of time, the pH value should be maintained at the above described level and the storage vessel is preferably a tightly capped polyethylene bottle or other inert plastic container which prevents the contents from absorbing carbon dioxide from the atmosphere.

The colloidal suspension of the reaction product is not suitable for use as a catalyst as prepared and it should be agitated sufficiently in the presence of a micelle-forming surfactant to form catalyst-containing micelles. The degree of agitation, the length of the agitation period, and the amount of the micelle-forming surfactant that is present in the colloidal suspension are controlled at levels favorable to the formation of micelles. For example, the surfactant may be present in an amount of about 0.001-0.1 mole per liter and preferably about 0.03-0.07 mole per liter for most surfactants. Smaller or larger amounts may be effective with some surfactants such as 0.0001 mole per liter or less, or 0.2 mole per liter or more. About 0.05 mole per liter often gives the best results with many surfactants.

The minimum period of agitation and the minimum degree of agitation that are required for micelle formation varies somewhat with temperature and the type and amount of surfactant. As is well understood in this art, gradually increasing these variants in the presence of an effective amount of the micelle-forming surfactant will result in micelle formation when the proper levels are reached. As a general rule, longer periods of agitation and/or more vigorous agitation are required to form micelles at lower temperatures approaching the freezing point of the colloidal suspension than at higher temperatures approaching the boiling point. In instances where the aqueous suspension has a temperature of approximately 50°-90° C., then mild agitation over a period of about 10-60 minutes is satisfactory. Often longer or shorter periods of mild to vigorous agitation may be employed such as from about 1-5 minutes to several hours at temperatures varying, respectively, between the boiling point and the freezing point. When desired, the agitation may be continued long after the catalyst-containing micelles are formed as continued agitation does not seem to have an adverse affect.

As a general rule, the micelle-forming surfactants known in the prior art may be used in practicing the present invention. Micelle-forming surfactants used in the emulsion polymerization of monomeric organic compounds are disclosed in the text *Synthetic Rubber*, by G. S. Whitby, et al, John Wiley & Sons Incorporated, New York (1954), and surface active agents in general are disclosed on pages 418–424 of the text *Organic Chemistry*, Fieser and Fieser, 2nd Edition, Reinhold Publishing Corporation, New York, New York (1950), the disclosures of which are incorporated herein by reference. Examples of surfactants disclosed in the above texts include the alkali metal soaps of long chain fatty acids, and especially the sodium and potassium soaps of fatty acids containing about 14–25 carbon atoms and preferably about 16–18 carbon atoms, and the sodium and potassium soaps of the rosin acids, abietic acid and the derivatives thereof. Other micelle-forming surfactants include fats and oils such as corn oil, cotton seed oil, castor oil, soy bean oil and safflower oil which have been fully or partially saponified with alkali metal bases to produce mixtures including saponified long chain fatty acids, the mono- or di-glycerides thereof, and glycerin.

Examples of synthetic micelle-forming surfactants include the sulfonates of long chain alcohols prepared by hydrogenation of naturally ocurring fats and oils of the above types and especially sulfonated long chain alcohols containing about 10–20 and preferably about 12–14 carbon atoms, the alkali metal salts of the monosulfonates of monoglycerides such as sodium glyceryl monolaurate sulfonate, the sulfonates of succinic acid esters such as dioctyl sodium sulfosuccinate and the alkylaryl alkali metal sulfonates. Specific examples of presently preferred micell-forming surfactants include sodium and potassium sulforicinoleate, tetrahydronaphthalene sulfonate, octahydroanthracene sulfonic acid, butyl naphthalene sulfonic acid, sodium xylene sulfonate, alkyl benzene sulfonic acid and potassium benzene sulfonate.

Sulfated long chain hydroxycarboxylic acids containing about 14–25 carbon atoms and preferably about 16–18 carbon atoms, and sulfated fats and oils containing hydroxycarboxylic acids of this type produce exceptionally good micelle-forming surfactants. At least 25% of the hydroxyl groups and preferably at least 50% should be sulfated, and up to 95–100% may be sulfated. It is usually preferred that the sulfated oils and/or long chain hydroxycarboxylic acids be neutralized with an alkali metal base, and that the corresponding alkali metal salts be added to the colloidal suspension in the form of an aqueous solution. The aqueous solution may contain at least 25% of water and preferably at least 35–40% by weight. Much larger percentages of water may be present when desired such as 75–80% or more by weight.

A very active catalyst is produced when using sulfated castor oil as the micelle-forming surfactant (Turkey Red oil). Sulfated castor oil which has been purified sufficiently to be of U.S.P. or medicinal grade produces an exceptionally active catalyst. For the best results, the castor oil is reacted with about an equal weight of concentrated sulfuric acid (e.g., 20% by weight $H_2SO_4$) at a temperature of approximately 25°–30° C. The mixture may be reacted for about two hours with stirring and is then neutralized with sodium hydroxide solution. The reaction mixture separates into three layers, i.e., an upper layer which is a water solution, an intermediate or oily layer, and a white curdy precipitate. The intermediate oily layer is separated from the upper and lower layers, and may be added to the colloidal suspension as the micelle-forming surfactant in an amount, for example, of 0.001–0.1 mole per liter, and preferably about 0.005 mole per liter.

The activity of the catalyst may be increased very markedly by cooling the aqueous catalyst suspension to a temperature approaching the freezing point such as about 0°–10° C., and then warming over one or more cycles. For best results, the aqueous catalyst suspension should be frozen and thawed over one or more cycles. The reason for the increased catalytic activity is not fully understood at the present time but cooling and then warming the aqueous catalyst suspension seems to increase the concentration of the catalyst-containing micelles and/or increases the catalytic activity thereof.

The aqueous suspension of the catalyst contains a relatively small percentage by weight of the active catalyst as produced. When desired, it may be concentrated by evaporating a portion of the water to produce a concentrated liquid catalyst suspension which may be stored and used more conveniently. It is also possible to prepare a dry catalyst concentrate by evaporating substantially all of the water. The preferred method of producing the dry catalyst concentrate is by flash evaporation using a technique analogous to that employed in preparing powdered milk. The catalyst concentrates produced upon partial or complete evaporation of the water content of the intially prepared aqueous suspension may be reconstituted by addition of water with little or no loss of catalytic activity. Preferably, the water is added to the dry catalyst concentrate under sufficiently vigorous conditions of agitation to assure that the catalyst micelles are resuspended and uniformly distributed.

In a further variant of the process for preparing the catalyst, at least one dissolved substance providing at least one amphoteric metal-containing ion is present in the aqueous medium at the time of reacting the alkali metal silicate with the substances providing calcium ion and magnesium ion. The substance or substances providing the amphoteric metal-containing ion or ions may be present, for example, in an amount sufficient to provide about 0.0001–10% and preferably about 0.01–0.5% by weight when calculated as the amphoteric metal oxide and based upon the weight of the alkali metal silicate. Preferred amphoteric metals include aluminum and/or zinc, and the preferred sources thereof include alkali metal aluminate and zincate of which sodium and/or potassium aluminate and/or zincate usually give the best results. The alkali metal aluminate and/or zincate may be added directly to the aqueous medium, or as the mineral acid salts, oxides and/or hydroxides which then form the alkali metal aluminate and/or zincate under the highly alkaline conditions that exist.

The aqueous catalyst suspension may be used in the concentration as produced, or it may be diluted with approximately 2–100,000 or more parts by weight of water prior to use. It is only necessary that the aqueous medium contain a catalytic amount of the catalyst and much larger than catalytic amounts may be present. For better results, in some instances the catalyst suspension as produced may be diluted with about 200–10,000 parts by weight of water, and for still better results in other instances, with about 500–1,000 parts by weight of water. The aqueous medium may, for example, have 0.000001–1% by weight and often about 0.0001–9.3% by weight of the catalyst, but larger or smaller amounts may be present. In some instances, the aqueous medium contains about 0.001–0.1% or 0.004–0.08% by weight of the catalyst, and in other instances about 0.006–007% by weight. The weight or weight percent of the catalyst is calculated on a dry solids basis, i.e., the total weight of the catalyst ingredients in the aqueous catalyst suspension as produced after removal of the water. The dry catalyst solids or liquid catalyst concentrate may be admixed with water and/or a micelle forming surface active agent to provide a catalytically effective catalyst micelle concentration such as in the quantities previously discussed. The pH of the diluted aqueous catalyst suspension to be used may be adjusted to a desired value by addition of a mineral acid such as sulfuric acid or a strong base such as alkali metal hydroxide. This variant is of importance when the catalyst suspension should be approximately neutral as used for a given purpose. This variant is also of importance where the aqueous catalyst suspension, when used for a specific purpose, should be strongly acidic or basic for better results.

The Preparation of Solutions Of Catalyst Treated Lignite

The aqueous solutions of catalyst treated lignite for use in practicing the method of the invention may be prepared as described hereinafter.

The lignite is intimately contacted in particulate form with an aqueous medium containing a catalytically effective amount of the novel catalyst described above. The lignite has active sites which are capable of reacting with at least one component of the aqueous medium in the presence of the catalyst, and it is contacted with the aqueous medium under liquid phase conditions until substantially all or a desired proportion of the active sites react. Thereafter, the lignite may be further treated as more fully described below.

The lignite need not be pretreated prior to treating with the aqueous medium other than, when desired, crushing or otherwise reducing it to a suitable particle size. The particle size is not critical and may vary over wide ranges as the aqueous medium has remarkable penetration properties and is capable of penetrating large lumps. The particle size may be, for example, from 1 inch to -300 mesh (Tyler Screen) and preferably is about -10 mesh to -200 mesh, and for many applications is from -50 mesh to -100 mesh. It is understood that particles as large as 2, 3 or 4 inches, and often mine run lignite, may be treated but longer periods of contact with the aqueous medium may be necessary to allow sufficient time for adequate penetration and reaction. Also, particle sizes smaller than -300 mesh may be treated but the expense of grinding the lignite to such a fine particle size usually outweighs any advantages that are gained. The volume ratio of aqueous medium to lignite may vary over wide ranges. It is usually preferred that the aqueous medium be present in sufficient volume to allow the particles to be easily agitated therein such as by means of a prior art stirring or agitating device. The concentration of the catalyst in the aqueous medium also may vary over wide ranges as it is only necessary that a catalytic amount be present. Suitable catalyst concentrations are discussed in the above section relating to the preparation of the catalyst. The pH value of the aqueous treating medium may vary from about 1 to 13.5. The initial pH value is preferably greater than 7, and is usually about 8–11. There is a tendency for the pH value to decrease as the reaction proceeds to about 5–6. If desired, the pH value of the aqueous medium may be adjusted as the reaction proceeds by addition of a base such as an alkali metal hydroxide to thereby partially or fully restore the initial pH value. Sodium, potassium or ammonium hydroxides are useful for this purpose and sodium hydroxide is usually preferred.

The temperature of treatment may likewise vary over wide ranges and may be, for example, between the freezing point and the boiling point of the aqueous medium under the existing pressure conditions. Usually atmospheric pressure is preferred, and in such instances, the aqueous medium may have a temperature of approximately 0° C. to 100° C. and is often about 20°–60° C. Surprisingly, lower temperatures of treatment such as 0°–10° C. appear to enhance the rate and degree of oxidation and thus lower temperatures may be preferred in instances where a maximum amount of oxidation is desired. Higher temperatures than 100° C. may be employed under superatmospheric pressure. Provided that the pressure is sufficient at the existing temperature to maintain liquid phase conditions, the temperature may be 100°–200° C. or higher but such extreme reaction conditions are not necessary and are usually avoided.

Inexpensive reaction vessels or open vats, with or without agitators and other simple auxiliary equipment, are satisfactory and may be used with good results. The period of treatment may be varied over wide ranges. It is only necessary that the aqueous medium be intimately contacted with the lignite for a period of time sufficient for the reaction to occur and continued treatment is not deleterious. The minimum period of treatment will vary to some extent with the remaining conditions, such as the particle size of the lignite, the concentration of the catalyst, the pH value of the aqueous medium and the reaction temperature. The period of treatment may vary, for example, from approximately 15 minutes or less to 24 hours or more but it is usually from about 1 to 3 hours. As a general rule, the amount of oxidation increases with time provided all of the remaining conditions of treatment remain the same. Lignite has active sites or carbon atoms such as carbon-to-carbon double or triple bonds, carbon-to-oxygen bonds, carbon-to-sulfur bonds, carbon-to-nitrogen bonds, carbon-to-metal bonds, carbon attached to an electro-negative group, and carbon bonded or otherwise attached or attracted to a dissimilar substrate which is a component of the lignite. The catalyst of the present invention causes the liquid water in the aqueous treating medium to exhibit very unusual and heretofore unrecognized properties in the presence of lignite having the aforementioned active carbon atoms or active sites. While the exact nature of the reaction is not known at the present time, it appears that water or some component of water reacts with or alters the active carbon atoms or active sites to thereby produce pronounced chemical and/or physical changes. For example, the lignite may be oxidized to produce carboxylic acids and especially humic acids. It is also possible to fix nitrogen in the presence of an atmosphere containing elemental nitrogen. Additionally, combustable sulfur, nitrogen, and deleterious substances in general are altered to permit their removal by prior art techniques such as by extraction in the aqueous treating medium or with solvents subsequent to the treatment. Additionally, metal values present in the lignite are rendered soluble or solubilized. The treated particles have a much higher water content than before treatment. Following treatment, the aqueous treating medium contains the water soluble constitutents of the treated lignite.

When the aqueous medium containing the catalyst is contacted with the lignite there is a period of activation during which there is little or no reaction. This activation period may be eliminated or reduced markedly by pre-treating a fresh catalyst suspension with a small portion of the lignite, or by using a recycled catalyst solution from a previous treatment. In a preferred variant, all or part of the aqueous catalyst suspension is recycled so that an activated catalyst is always available for contacting with fresh portions of the lignite. The activated aqueous catalyst suspension thus produced is much more effective.

In a further variant of the invention, the lignite is treated with an oxidizing agent before, during or following treatment with the aqueous medium containing the catalyst. The oxidizing agent may be air, elemental oxygen, ozone, peroxides such as hydrogen peroxide or the alkali metal peroxides, or other suitable oxidizing agents. The lignite is reacted with the oxidizing agent in an amount to partially oxidize or artificially weather it without combustion. For example, air or elemental oxygen may be bubbled through the aqueous medium while in contact with the lignite, or the lignite may be intimately contacted with air or elemental oxygen at elevated temperature prior to treatment with the aqueous medium. The oxidation of the lignite often may be enhanced by treating with the aqueous catalyst suspension at temperatures approaching the freezing point, such as about 0°–10° C. and preferably about 0°–4° C. The degree of oxidation is also often controlled to some extent by the materials used in constructing the reaction vessel and the materials of construction of auxiliary apparatus in contact therewith such as agitators. Surprisingly, constructing the equipment from nonconductors of electricity such as polyolefins results in a maximum degree of oxidation under a given set of operating conditions. Constructing the equipment from good conductors of electricity such as steel and other metals results in a minimum degree of oxidation for a given set of treating conditions, whereas constructing the equipment from glass or ceramic materials results in an intermediate degree of oxidation.

It is not necessary to separate the catalyst suspension from the treated lignite. For example, in many instances it is advantageous to evaporate the water content of the aqueous suspension, either at atmospheric pressure or preferably under reduced pressure, to thereby deposit the catalyst micelles on the treated lignite. When this is done, addition of water reactivates the catalyst micelles and the lignite may be subjected to a further treatment with the aqueous catalyst suspension until it is fully solubilized.

It is understood that the lignite is treated with an aqueous catalyst suspension until it is solubilized therein. The terms "solution," "solubilized," etc., as used herein when referring to this product are intended to embrace true solutions as well as aqueous media containing finely divided suspended substances which are not in true solution. It is also understood that the lignite solution, which contains the novel catalyst suspension described hereinbefore as an ingredient, may be substituted for the aqueous catalyst suspension per se in the method of the invention. It is only necessary to substitute a like amount of the catalyst-containing lignite solution for the aqueous catalyst suspension per se, based upon the dry solids weight of the catalyst present in each instance.

In practicing one presently preferred variant, the lignite is treated initially with the aqueous catalyst suspension following the aforementioned general procedure to produce a catalyst treated lignite product. This initial treatment may involve admixing the particulate lignite with the aqueous catalyst suspension and allowing it to soak at ambient temperature for a substantial period of time such as 1–24 hours and preferably for about 15 hours. While this initial soaking period is not essential, it appears to improve the uniformity of the results without producing adverse effects in instances where it is not needed. The initial pH value of the admixture is approximately 8–11, and during the soaking period, the pH value gradually drops to approximately 4–6.5 and preferably about 5–6. The admixture is then heated to an elevated temperature such as about 60°–100° C. and preferably about 90°–100° C. with stirring for approximately 0.5–5 hours and for best results approximately 1–3 hours. Thereafter a strong base such as sodium hydroxide is added in an amount to adjust the pH to the initial value of approximately 8–11 and preferably about 9–10, followed by continued heating with agitation until the pH value gradually drops again to approximately 4–6.5 and preferably about 5–6. In instances where the pH value remains above this latter range, then additional untreated lignite may be added in an amount to lower the pH level. The water is evaporated from the admixture without filtering as valuable ingredients are dissolved in the aqueous treating medium. Conventional air drying at ambient or elevated temperature or vacuum drying is usually preferred. The dry catalyst treated lignite product has the catalyst micelles initially present in the aqueous treating medium deposited thereon and it may be stored for long periods of time while awaiting further treatment and use. The aqueous catalyst suspension used in the aforementioned initial treatment of the lignite is preferably concentrated and may be a catalyst suspension as produced by Examples I–IV appearing hereinafter.

The dry catalyst treated lignite thus prepared may be admixed with additional aqueous catalyst suspension, which also is preferably concentrated and may be as produced by Examples I–IV, in an amount to prepare an oily paste-like admixture. Approximately equal parts by weight of the catalyst treated lignite and aqueous catalyst suspension usually produce good results. This paste-like admixture may be easily dissolved in water and/or diluted catalyst suspension in amounts to produce a solution containing the desired amounts of dissolved lignite and/or catalyst on a dry solids basis for use in a given environment. It is only necessary that the catalyst be present in the catalytic amounts as described hereinbefore in the section on catalyst preparation, and the concentration of dissolved lignite may be as described below.

The concentrations of the catalyst suspension and the dissolved lignite solids in the solution may vary over extremely wide ranges. In a number of instances, the concentrations thereof are determined to some extent by the specific end use of the solution. Also, it is often advantageous to provide a concentrated solution which is diluted at the time of use. As a general rule, the concentration of catalyst solids in the solution is within the ranges aforementioned in the section on the preparation of the catalyst. The concentration of dissolved lignite in the solution may vary from about 0.01 to 0.1 part per million up to about 10% to 20% by weight. Solutions containing at least 500 parts per million, and preferably at least 600-700 parts per million, of dissolved lignite exhibit pronounced bacteriostatic and/or fungistatic properties and are often preferred for this reason. Solutions for general use usually contain about 0.5-500 parts per million, and preferably about 100-200 parts per million, of dissolved lignite and catalyst solids within the preferred ranges aforementioned, although more concentrated solutions may be provided initially for dilution. As a general rule, the solutions usually contain about 1-2% by weight or less of dissolved lignite.

Some naturally occuring lignites contain metal values or other substances which are undesirable when the lignite solutions are used for certain purposes such as in animal feeds, drinking water, medicinals and the like. In a further variant of the invention, the undesirable substances are removed from the lignite and/or rendered soluble in an extraction solvent in a pretreatment step with the catalyst suspension. For example, the lignite may be treated with an aqueous suspension of the catalyst following the usual practice until the undesirable substances are solubilized in the aqueous medium or rendered soluble in an extraction solvent. The period of treatment to accomplish this purpose may vary over wide ranges, such as from about 10 minutes to 10 hours or longer, or until the particles of lignite take on a weathered appearance similar to Leonardite and yet remain insoluble in the aqueous catalyst suspension and the extraction solvent. The treated lignite is separated from the catalyst suspension to thereby remove water soluble undesired substances. If water insoluble undesired substances are present, they may be removed by extraction with a suitable solvent. For example, aqueous mineral acids such as hydrochloric and sulfuric acid solutions may be used to remove acid soluble undesired constituents. Similarly, aqueous bases such as sodium, potassium and ammonium hydroxide may be used to remove undesired substances which are soluble in alkaline solutions. Additionally, liquid organic solvents such as liquid hydrocarbons, chlorinated hydrocarbons, alcohols, ketones and esters may be used to extract organic solvent soluble undesired substances. The resultant extracted lignite, which is now substantially free of undesired substances, is then further treated with the aqueous catalyst suspension until it is solubilized and a solution thereof may be prepared as previously discussed.

The concentrations of the catalyst and thes solubilized lignite in the lignite solution are calculated by weight and on a dry solids basis. The lignite solids should be thoroughly air dried before washing.

The invention is further illustrated by the following specific examples, whch are for purposes of illustration only and are not limiting to the spirit or scope of the appended claims.

EXAMPLE I

This example illstrates one presently preferred process for preparing the novel catalyst used in practicing the invention.

Anhydrous calcium chloride in an amount of 0.66 gram and magnesium sulfate heptahydrate in an amount of 1.32 grams were dissolved in 2 liters of deionized water with stirring and warming until solution was complete. Then 95 grams of sodium silicate pentahydrate having a molecular ratio of sodium oxide to silicon dioxide of 1:1 were added to the solution with stirring and continued warming to produce a white colloidal suspension of the reaction product.

After setting for 10 minutes, the colloidal suspension was heated to 80° C. and sulfated castor oil in an amount of 201 grams was added with stirring. The average molecular weight of the sulfated castor oil was 940 and it contained 50% of water. The turbidity lessened somewhat as the colloidal suspension was heated at 80°-90° C. for 1 hour with vigorous stirring to produce catalyst micelles. The aqueous suspension of catalyst micelles thus prepared had a viscosity similar to that of water and it was used as a catalyst as noted hereinafter.

A dry or solid catalyst concentrate was prepared in a further run by evaporating water from the initially prepared aqueous catalyst suspension. The resulting dry catalyst concentrate was resuspended in water and there was no substantial loss of catalytic activity. In still other runs, the catalytic activity of the aqueous suspension of catalyst as initially prepared, the diluted aqueous suspension of catalyst, and the reconstituted aqueous catalyst suspension was enhanced by freezing and thawing.

EXAMPLE II

This example illustrates the preparation of additional catalyst suspensions.

Five suspensions of the catalyst were prepared from the same ingredients as used in Example I and following the general procedure of Example I. The ratios of ingredients were varied as follows:

| Ingredient | Amount of Ingredient | | | | |
| --- | --- | --- | --- | --- | --- |
|  | Run 1 | Run 2 | Run 3 | Run 4 | Run 5 |
| Deionized water | 2 l | 1.5 l | 1.5 l | 1.5 l | 0.25 l |
| $CaCl_2$ | 0.66 g | 0.5 g | 0.5 g | 1.0 g | 0.5 g |
| $MgSO_4 \cdot 7H_2O$ | 1.32 g | 1.0 g | 1.0 g | 2.0 g | 1.0 g |
| $Na_2SiO_3 \cdot 5H_4O$ | 165 g | 132 g | 71 g | 185 g | 71 g |
| Sulfated Castor oil (approximately 50% by weight $H_2O$) | 100 ml | 150 ml | 150 ml | 200 ml | 150 ml |

The catalyst suspensions prepared by the above five runs were used as noted hereinafter.

EXAMPLE III

This Example illustrates a further presently preferred process for preparing the catalyst of the invention.

Anhydrous calcium chloride in an amount of 0.66 gram and magnesium sulfate heptahydrate in an amount of 1.32 grams were dissolved in 1 liter of soft water heated to 80° C. Then 95 grams of sodium silicate pentahydrate was added to the resulting solution with stirring to produce a suspension of finely divided particles of the reaction product. The sodium silicate pentahydrate contained approximately 0.12 gram of alluminum when calculated as $Al_2O_3$ and a somewhat smaller amount of zinc when calculated as ZnO.

The suspension of the reaction product was maintained at 80° C. and stirred for one-half hour. Then an aqueous solution prepared by admixing 75 grams of sulfated castor oil with 100 milliliters of water was added slowly with stirring. The stirring was continued for one-half hour thereafter while maintaining the reaction mixture at 80° C. to produce catalyst-containing micelles.

The sulfated castor oil contained 6.5-7% of organically combined SO₃ on a dry basis, 0.9-1.1% of combined alkali when calculated as sodium oxide, no free alkali, and 50% ± 1% of material volatile at 105° C., which was mostly water. The average molecular weight of the sulfated castor oil molecule was approximately 400 grams per mole.

The above prepared suspension of catalyst was placed in plastic containers awaiting testing and use. The catalyst suspension was tested and was rated as a suspension catalyst. It was possible to add from 1,000 to 10,000 parts of water to a portion of the catalyst suspension and still obtain excellent catalytic activity. A further portion of the catalyst suspension was frozen and thawed, and then tested. The cooling and warming steps enhanced the catalytic activity.

EXAMPLE IV

The general procedure of Example III was followed with the exception of using 0.33 gram of anhydrous calcium chloride rather than 0.66 gram, 0.66 gram of magnesium sulfate heptahydrate rather than 1.32 grams, and 45 grams of sodium silicate pentahydrate rather than 95 grams. The remaining ingredients and steps in the Example III procedure for preparing the catalyst were not changed.

The resulting catalyst suspension was approximately one-half as concentrated as that prepared in Example III. Upon testing, it was found to be as effective as the catalyst of Example III when calculated on a dry solid basis. Cooling the catalyst suspension to temperatures approaching the freezing point or freezing, followed by warming or thawing, also had a beneficial effect upon the catalytic activity.

EXAMPLE V

This example illustrates the preparation of solutions from lignite which are useful in practicing the method of the invention.

Lignite from the Havelock Mine, New England, North Dakota was ground to minus 60 mesh (Tyler Screen) and 200 grams thereof was admixed with 250 ml of a catalyst suspension prepared in accordance with Example I and diluted with 100 volumes of water. The admixture was treated for 2 hours at room temperature (72° F.) in a 1 quart Abbe Ball Mill using ⅜ inch ceramic balls. Following the treatment, the reaction mixture was filtered to obtain a glassy black pitch-like solid residue of treated lignite particles and a yellow liquid treating solution having a pH of 6.7.

The treated lignite particles were extracted with acetone to produce a dark red solution and a residue of acetone extracted particles. The acetone extracted particles were further extracted with 3 M hydrochloric acid to obtain a yellow-orange acidic extract solution and an acid extracted residue.

The acid extracted char was further treated with 1 M sodium hydroxide solution and the mixture set to a jet-black pitchlike substance. The solution was filtered with difficulty to yield a black thin liquid and a sodium hydroxide treated residue. When the residue was washed with water, the solid material peptized and passed through the filter. Thus, substantially all of the lignite was solubilized.

EXAMPLE VI

This Example illustrates the preparation of an aqueous solution of catalyst treated lignite.

Weathered lignite having a particle size of −80 mesh (Tyler Screen) was admixed in an amount of 50 pounds with 2.50 ml of the catalyst suspension prepared in accordance with Example I and 8 gallons of hot soft water having a temperature of 150° F. The admixture was heated and stirred and after five minutes, the pH value was approximately 5. The admixture was allowed to set without heating for 12 hours and then 2 pounds of flake caustic (78% sodium hydroxide) was added. The admixture was stirred for approximately 5 minutes and the pH was 5-6. The wet catalyst treated lignite was air dried and stored in a plastic container.

The above prepared catalyst treated lignite was admixed in an amount of 298 grams with 307 grams of the catalyst suspension prepared in accordance with Example I. The resultant moist solid was stored in airtight container while awaiting the preparation of a solution. Thereafter, 5 grams of this admixture was added to one gallon of soft water. Substantially all of the treated lignite dissolved forming a dark opaque blue-black solution. The solution contained the catalyst in a concentration equivalent to diluting the catalyst suspension of Example I with 100 volumes of water and it also contained 700 parts per million of the dissolved catalyst treated lignite. The pH value was 7.

EXAMPLE VII

This Example illustrates the treatment of lignite from Havelock Maine, New England, North Dakota having a particle size such that 85% passed through a −85 mesh Tyler Screen.

An admixture of 70 pounds of the lignite, 300 ml of the catalyst suspension prepared in accordance with Example I and 8 gallons of soft water having a temperature of 150° F. was prepared. After 5 minutes of heating and stirring, the pH was 5 and 2.2 pounds of flake caustic sode (78% sodium hydroxide) was added. The pH of the resultant solution was 12 and after one-half hour of heating the pH was 11. The admixture was allowed to set for 12 hours.

Thereafter ⅓ of the treated lignite was air dried. A white encrustation appeared on the surface after drying. A second ⅓ portion of the treated lignite was kept moist with water for 2 days to determine if air oxidation continues provided the treated lignite is kept moist and basic. Upon testing, it was found that the air oxidation did continue. A white encrustation formed on the surface of the treated lignite when dry. The remaining ⅓ portion of the treated lignite was admixed with 2 gallons of hot soft water and thereafter 100 grams of sodium perborate was added. The temperature was 76° C. Thereafter, the treated lignite was air dried in the sun and no white encrustation developed on the surface. Lignite solutions are prepared from each of the above dry catalyst treated lignite produces following the general procedure set out in the last paragraph of Example VI.

EXAMPLE VIII

This Example illustrates a further presently preferred process for preparing aqueous solutions of lignite which are useful in practicing the method of the invention.

Fifty pounds of North Dakota lignite was ground to −80 Tyler Mesh and admixed with 5 gallons of softened water containing 100 ml of the concentrated aqueous catalyst suspension as produced by Example I. The admixture was allowed to soak without heating for 15 hours. At the end of the soaking period, the pH value was 5 and the admixture was heated at 90°–100° C. with stirring for 3 hours. Sufficient flake sodium hydroxide was added to adjust the pH value to 11 and the heating and stirring was continued until the pH value had decreased to 5.

The water was removed from the resultant aqueous admixture of catalyst treated lignite by air drying. The dry catalyst treated lignite product thus prepared was stored in containers while awaiting the preparation of lignite solutions.

Approximately equal parts by weight of the catalyst treated air dried lignite and of the concentrated catalyst suspension prepared by Example I were admixed to produce a solid material having a paste-like consistency. Aqueous solutions of catalyst treated lignite were prepared from the paste having the following formulations:

TABLE I

| Formulation No. | 1 | 2 | 3 | 4 |
|---|---|---|---|---|
| Ingredient | | | | |
| Catalyst Treated Lignite paste, grams | 7.32 | 2.9 | 300 | 300 |
| Concentrated Catalyst Suspension prepared by Example I, liters | None | 2.4 | 1.0 | 2.0 |
| Soft water, liters | 3.875 | 16.0 | 17.4 | 16.4 |

Certain of the above formulations were used in examples as noted hereinafter.

Additional solutions of catalyst treated lignite are prepared in further runs by following the general procedure of this Example with the exception of substituting the catalyst suspensions prepared in accordance with Examples II, III and IV for the catalyst suspension of Example I. All of the catalyst suspensions are active and are useful in solubilizing the lignite. Comparable results are obtained when the amount of the catalyst to be used is based upon dry catalyst solids.

Formulation No. 1 has strong germicidal and fungicidal properties and is especially useful in cleansing and disinfecting cuts, wounds and open sores, and in the treatment of fungus infections. This formulation also is useful as a de-wormer for poultry and livestock such as horses, cows, sheep and pigs.

Formulations No. 2, 3 and 4 are useful in a number of applications. These formulations are usually diluted markedly prior to use in drinking water, and when the formulations are to be administered orally or parenterally. The presently preferred dilution of Formulations 2–4 for many uses is at the rate of 1 ounce for each gallon of water, but much higher or lower concentrations may be used in many applications. For example, Formulations 1–4 may be diluted at the rate of one volume for each 1–1000 volumes of water, and for better results in many instances at the rate of one volume for each 10–200 volumes of water, or at the rate of one volume for each 100–150 volumes of water. When used in drinking water, for example, Formulations 1–4 may be diluted at the rate of one volume for each 50,000–500,000 volumes of water, and preferably at the rate of one volume for each 90,000–300,000 volumes of water. Thus, it is apparent that the treating solution to be used in a given application need contain only a catalytic quantity of the catalyst and an effective but usually correspondingly small amount of the catalyst treated lignite, which also may be present in substantially catalytic quantities.

EXAMPLE IX

This Example illustrates the use of lignite solutions prepared in accordance with Example VIII in general veterinary practice to relieve stress and shock and promote the healing of infected or damaged tissue in domestic animals.

The veterinarian had a practice consisting of approximately 60% of large animals such as horses and cows, and 40% of small animals such as dogs and cats. In a first series of tests, Formulation No. 1 of Example VIII was used to cleanse and disinfect open sores and wounds, including cuts caused by wire, accidents in general, and incisions made during surgery. Following stitching of the cleaned and disinfected cuts or incisions, the formulation was applied topically by spraying, followed by additional topical applications one to three times per day. No further treatment was given with the exception of cleaning the damaged area where necessary to allow the formulation to be topically applied. The animals were observed closely for side effects and to determine the rate of healing. There was a marked reduction in inflammation and also a very definite reduction of capillary hemorrhage with no adverse side effects. In instances where an animal was initially under stress and/or shock due to an injury or surgery, it was further observed that both stress and shock were relieved. The animal was calm and tranquil following the application of the formulation without the need for administering drugs.

The infected or damaged tissue in animals treated with the formulation healed at a much more rapid rate than in a control group of animals where conventional veterinary practice was followed. In addition to reducing inflammation and hemorrhage, there was also a very desirable debriding effect without decreasing the healing rate. The debriding action allowed the fresh viable tissue to heal without an overrun of proud flesh. There was much less pain and the animals remained calm and had a tranquil attitude during treatment.

In a further series of experiments. Formulations 2, 3 and 4 were diluted with water to provide a treating solution containing 1 ounce of the formulation per gallon of water. The diluted formulation was applied to animals having damaged and/or infected tissue, including open sores, cuts, bruises, sprains and surgical incisions, three times a day by spraying the affected area. No further treatment was given with the exception of the usual cleansing of the damaged or infected area where necessary to allow the formulation to be topically applied. The rate of healing was observed closely, and was found to be at a much more rapid rate than in a control group of animals where conventional veterinary practice was followed. There was reduced inflammation and capillary hemorrhage, and a desirable debriding action, but not as pronounced as in the first series of experiments with Formulation No. 1. Also, stress and shock were relieved without the need for administering drugs.

In a third series of experiments, a large number of cattle were treated parenterally with a synergistic mixture containing a water based antibiotic and approximately an equal volume of Formulation No. 3 diluted with water at the rate of one pint for each five gallons of water. The antibiotics included Combiotic ®, which is a mixture of penicillin and dihydrostreptomycin, Penstrep, and numerous other broad spectrum antibiotics. The animals were injected intramuscularly with 20–40 cc, depending on size, of the antibiotic and an equal volume of the diluted Formulation No. 3 in the treatment of diseases such as scours, dust pneumonia, cancer eye and foot rot. The injections were given daily over several days until a cure was effected and the results were observed and compared with a control group of animals which received only the antibiotic.

There was a definite synergistic action in instances where the animals were injected with a mixture of the antibiotic and diluted Formulation No. 3. The initial response to the antibiotic was much faster, less antibiotic was required to achieve a cure, and no side effects were observed. The animals receiving the synergistic admixture would drink water much more affluently thus establishing their elecrolytic balance with greater ease. This also contributed to the rate of cure and the overall well being of the animals.

In a fourth series of experiments, Formulation No. 3 of Example VIII was diluted with water at the rate of one pint for each five gallons. The resultant diluted solution was used as a synergist or adjuvant in the treatment of animals having diseases which respond to treatment with water based formulations of sulfur drugs, electrolytes in general, and Cal-Dextro and glucose combinations specifically, which are given intraveneously. Conventional practice was followed with the exception of also using an equal volume of diluted Formulation No. 3. No adverse side effects were noted. The response to the therapeutic treatment in each instance was much more rapid, less of the drug was needed for a given degree of effectiveness, and the cure rate was higher than in a control group of animals which did not receive the diluted Formulation No. 3.

In a fifth experiment, a calf having severe scours was drenched with 10 ounces of the diluted Formulation No. 3 described above, and then treated intraveneously with 20 cc of the diluted Formulation No. 3. The calf recovered at a rate far faster than was though possible in view of the severity of the calf's initial condition.

In a sixth series of experiments, cattle having pink eye was treated with the diluted Formulation No. 3 described above topically and parenterally. The infected area was sprayed topically one to three times per day with the diluted Formulation No. 3, and once daily the cattle were injected intramuscularly with 20-40 cc of the diluted Formulation No. 3 depending upon size. The pink eye was cured much faster and with a far higher rate of cure than when using conventional veterinary practice.

In a seventh rate series of experiments, cattle which had been subjected to a long haul following a sale was under extreme stress, and also several animals were infected with hemorrhagic septicemia and other diseases. The cattle were treated by oral administration of the above described diluted Formulation No. 3 in drinking water. One ounce of the diluted Formulation No. 3 was used to treat each 20 gallons of drinking water. The cattle returned to drinking water readily, which is unusual under such conditions, and continued to drink sufficient water to overcome dehydration. The cattle also started eating and had a much more tranquil attitude. There was no loss of animals as often occurs under these conditions. No adverse side effects of the treatment were observed.

EXAMPLE X

A rancher had several calves which contracted dust pneumonia. Some of the calves were infected so badly that they could not nurse and several were unable to walk.

Formulation No. 2 of EXAMPLE VIII was diluted with water at the rate of one ounce per gallon of water and the resultant diluted formulation was used in the treatment of the calves. The calves were drenched with 8-10 ounces of the diluted formulation, and were then given an intramuscular injection of 20 cc of Combiotic and 20 cc of the diluted Formulation No. 2. The calves responded dramatically to the combination of oral administration and intramuscular injection, and were up and nursing and well on their way to recovery within 24 hours.

EXAMPLE XI

A rancher had a large number of cattle with diseases such as scours, water belly and red nose. The cattle were drenched with 4-16 ounces, depending on size, of Formulation No. 2 of Example VIII diluted with water at the rate of 1 ounce per gallon of water. The cattle responded favorably and without side effects. In severe cases, the cattle were also injected intramuscularly with 20-40 cc, depending on size, of a diluted Formulation No. 3 of Example VIII, which was diluted at the rate of one pint for each 5 gallons of water. The combination of oral administration and intramuscular injection resulted in a marked further improvement in the rate of cure.

EXAMPLE XII

This Example illustrates the use of a treating solution in relieving stress and shock in weaned calves. The solution was prepared by diluting Formulation No. 2 of Example VIII at the rate of one ounce per gallon of water.

Prior to or immediately following weaning, the calves were placed on drinking water containing one ounce of the diluted Formulation No. 2 in 20 gallons of drinking water. The calves were kept on the treated drinking water for several weeks following weaning. During this time, the calves did not contact the usual diseases which weaned calves are commonly subjected to, such as dust pneumonia, water belly, scours and the like. Also, the calves were noticeably freer from the stress associated with weaning. They ate specially prepared feed earlier and much more freely than in a control group which did not receive the treated water. No calves were lost from the group receiving the treated drinking water, whereas up to 20% of weaned calves are often lost when following conventional prior art weaning practice. It was apparent that the treated drinking water not only relieved stress and shock, but also enabled the calves to digest the specially prepared weaning food more easily and completely.

EXAMPLE XIII

Calves to be branded and dehorned were separated into two groups. The first group was used as a control group, and the usual ranch practice was followed subsequent to branding and dehorning. The control group of calves had unhealed wounds resulting from the branding and dehorning for up to six weeks.

A second group of calves were branded and dehorned following the same practice as used on the first group with the exception of spraying the open wounds one to three times per day with a diluted Formulation No. 3 prepared in accordance with Example VIII. Formulation No. 3 was diluted at the rate of 1 pint for each 5 gallons of water, and the diluted formulation was applied topically one to three times per day by spraying. After each application, the treated calves were calm and stress and shock were relieved. The calves also did not appear to be in pain. After several days of this treatment, the wound from the branding and dehorning had healed without loss of calves.

EXAMPLE XIV

This Example illustrates the synergistic effect of Formulation No. 3 when used in combination with antibiotics in the treatment of cancer eye in cattle.

Formulation No. 3 of Example VIII was diluted with water at the rate of one pint for each five gallons of water. The resultant diluted Formulation No. 3 was then used in this Example.

Cattle infected with cancer eye were injected intramuscularly with 20 cc of Combiotic and 20 cc of the diluted Formulation No. 3 daily for 2 days. The diluted Formulation No. 3 was also applied topically to the infected area by spraying one to three times per day for 10 days.

The cattle were observed over the 10 day period of treatment and the cure rate was found to be in excess of 50%. A cure rate in excess of 50% is considered to be remarkable in the treatment of cancer eye.

EXAMPLE XV

The test procedures of Examples IX through XIII are repeated with the exception of using the catalyst suspensions prepared by the procedures of Examples II–IV in the preparation of lignite solutions in accordance with the procedures of Examples VI through VIII. Comparable results to those reported in Examples IX through XIII are obtained.

I claim:

1. A therapeutic composition for treating warm blooded animals having damaged or infected tissue which responds to treatment with an antibiotic comprising a therapeutically effective amount of an antibiotic which is therapeutically effective in treating the said damaged or infected tissue, a catalytically effective amount of a catalyst, and a therapeutically effective amount of water soluble catalyst treated lignite;

the said catalyst being prepared by a process comprising admixing a water soluble alkali metal silicate with an aqueous medium containing a dissolved substance which is a source of calcium ion and a dissolved substance which is a source of magnesium ion;

the aqueous medium containing said dissolved substances in amounts to provide between about $1 \times 10^{-4}$ and $1 \times 10^{-1}$ mole per liter each of calcium ion and magnesium ion, the aqueous medium containing said dissolved substances in amounts to provide a molar ratio of calcium ion to magnesium ion between about 2.0:1.0 and 1.0:2.0, the alkali metal silicate having an alkali metal oxide to silicon dioxide ratio between about 0.9:1.0 and less than 2.0:1.0 and being admixed with the aqueous medium in an amount of about 0.05–2 moles per liter, reacting the alkali metal silicate with said dissolved substances providing calcium ion and magnesium ion to produce an aqueous suspension of finely divided particles of the reaction product, admixing a micelle-forming surfactant with the aqueous medium in an amount to form catalyst micelles comprising said finely divided particles of the reaction product upon agitating the aqueous medium, and agitating the aqueous medium containing the finely divided particles of the reaction product and surfactant to form said catalyst micelles; and the said catalyst treated lignite being prepared by a process comprising intimately contacting solid lignite in particulate form with a liquid aqueous medium containing a catalytically effective amount of the said catalyst, the said particles of the lignite having active sites therein which react with at least one component of the said aqueous medium containing the catalytically effective amount of the catalyst under liquid phase conditions and in the presence of the said catalyst, and the said particles of the lignite being intimately contacted under liquid phase conditions until the active sites thereof react with at least one component of the said aqueous medium containing the catalytically effective amount of the catalyst and until the lignite is soluble in an aqueous medium.

2. The composition of claim 1 wherein in the process for preparing the catalyst, said ratio of calcium ion to magnesium ion is between about 1.5:1.0 and 1.0:1.5.

3. The composition of claim 1 wherein in the process for preparing the catalyst, said ratio of calcium ion to magnesium ion is about 1.0:1.0.

4. The composition of claim 1 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion.

5. The composition of claim 1 wherein in the process for preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion.

6. The composition of claim 1 wherein in the process for preparing the catalyst, about 0.2–0.5 mole per liter of the alkali metal silicate is admixed with the aqueous medium.

7. The composition of claim 1 wherein in the process for preparing the catalyst, the alkali metal silicate has an alkali metal oxide to silicon dioxide ratio between about 0.9:1.0 and 1.2:1.0.

8. The composition of claim 1 wherein in the process for preparing the catalyst, the alkali metal silicate is alkali metal metasilicate having an alkali metal oxide to silicon dioxide ratio of about 1.0:1.0.

9. The composition of claim 1 wherein in the process for preparing the catalyst, about 0.01–0.1 mole per liter of the surfactant is admixed with the aqueous medium.

10. The composition of claim 1 wherein in the process for preparing the catalyst, the surfactant comprises sulfated castor oil.

11. The composition of claim 1 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion, the ratio of calcium ion to magnesium ion is between about 1.5:1.0 and 1.0:1.5, about 0.2:0.5 mole per liter of the alkali metal silicate is admixed with the aqueous medium, and the alkali metal silicate has an alkali metal oxide to silicon dioxide ratio between about 0.9:1.0 and 1.2:1.0.

12. The composition of claim 1 wherein in the process of preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion, the aqueous medium contains about equimolar amounts of calcium ion and magnesium ion, about 0.2–0.3 mole per liter of the alkali metal silicate is admixed with the aqueous medium, and the alkali metal silicate is alkali metal metasilicate having an alkali metal oxide to silicon dioxide ratio of about 1.0:1.0.

13. The composition of claim 12 wherein in the process for preparing the catalyst, the alkali metal metasilicate is sodium metasilicate having a sodium oxide to silicon dioxide ratio of about 1.0:1.0.

14. The composition of claim 12 wherein in the process for preparing the catalyst, about 0.01–0.1 mole per liter of the surfactant is admixed with the aqueous medium.

15. The composition of claim 14 wherein in the process for preparing the catalyst, the surfactant comprises sulfated castor oil.

16. The composition of claim 15 wherein in the process for preparing the catalyst, the alkali metal metasilicate is sodium metasilicate having a sodium oxide to silicon dioxide ratio of about 1.0:1.0.

17. The composition of claim 16 wherein in the process for preparing the catalyst, at least 50% of the hydroxy groups of the castor oil are sulfated, and about 0.03–0.07 mole per liter of the sulfated castor oil is admixed with the aqueous medium.

18. The composition of claim 12 wherein in the process for preparing the catalyst, the alkali metal silicate is admixed with an aqueous medium containing said dissolved substances in amounts to provide about $2.9 \times 10^{-3}$ mole per liter of calcium ion and about $2.7 \times 10^{-3}$ mole per liter of magnesium ion, about 0.25 mole per liter of sodium metasilicate having a sodium oxide to silicon dioxide ratio of about 1.0:1.0 is admixed with the aqueous medium, the aqueous medium contains not more than 10 parts per million by weight of carbonate ion and bicarbonate ion, the surfactant comprises sulfated castor oil and at least 50% of the hydroxy groups of the castor oil are sulfated, and about 0.05 mole per liter of the sulfated castor oil is admixed with the aqueous medium.

19. A method of therapeutically treating a warm blooded animal having damaged or infected tissue which responds to treatment with an antibiotic comprising treating the warm blooded animal with a therapeutic composition containing an antibiotic in the presence of a catalyst and catalyst treated lignite, the said catalyst being prepared by a process comprising admixing a water soluble alkali metal silicate with an aqueous medium containing a dissolved substance which is a source of calcium ion and a dissolved substance which is a source of magnesium ion;

the aqueous medium containing said dissolved substances in amounts to provide between about $1 \times 10^{-4}$ and $1 \times 10^{-1}$ mole per liter each of calcium ion and magnesium ion, the aqueous medium containing said dissolved substances in amounts to provide a molar ratio of calcium ion to magnesium ion between about 2.0:1.0 and 1.0:2.0, the alkali metal silicate having an alkali metal oxide to silicon dioxide ratio between about 0.9:1.0 and less than 2.0:1.0 and beng admixed with the aqueous medium in an amount of about 0.05–2 moles per liter, reacting the alkali metal silicate with said dissolved substances providing calcium ion and magnesium ion to produce an aqueous suspension of finely divided particles of the reaction product, admixing a micelle-forming surfactant with the aqueous medium in an amount to form catalyst micelles comprising said finely divided particles of the present product upon agitating the aqueous medium, and agitating the aqueous medium containing the finely divided particles of the reaction product and surfactant to form said catalyst micelles; and the said catalyst treated lignite being prepared by a process comprising intimately contacting solid lignite in particulate form with a liquid aqueous medium containing a catalytically effective amount of the said catalyst, the said particles of the lignite having active sites therein which react with at least one component of the said aqueous medium containing the catalytically effective amount of the catalyst under liquid phase conditions and in the presence of the said catalyst, and the said particles of the lignite being intimately contacted under liquid phase conditions until the active sites thereof react with at least one component of the said aqueous medium containing the catalytically effective amount of the catalyst and until the lignite is soluble in an aqueous medium.

20. The method of claim 19 wherein in the process for preparing the catalyst, said ratio of calcium ion to magnesium ion is between about 1.5:1.0 and 1.0:1.5.

21. The method of claim 19 wherein in the process for preparing the catalyst, said ratio of calcium ion to magnesium ion is about 1.0:1.0.

22. The method of claim 19 wherein the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion.

23. The method of claim 19 wherein in the process for preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion.

24. The method of claim 19 wherein in the process for preparing the catalyst, about 0.2–0.5 mole per liter of the alkali metal silicate is admixed with the aqueous medium.

25. The method of claim 19 wherein in the process for preparing the catalyst, the alkali metal silicate has an alkali metal oxide to silicon dioxide ratio between about 0.9:1.0 and 1.2:1.0.

26. The method of claim 19 wherein in the process for preparing the catalyst, the alkali metal silicate is alkali metal metasilicate having an alkali metal oxide to silicon dioxide ratio of about 1.0:1.0.

27. The method of claim 19 wherein in the process for preparing the catalyst, about 0.01–0.1 mole per liter of the surfactant is admixed with the aqueous medium.

28. The method of claim 19 wherein in the process for preparing the catalyst, the surfactant comprises sulfated castor oil.

29. The method of claim 19 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion, the ratio of calcium ion to magnesium ion is between about 1.5:1.0 and 1.0:1.5, about 0.2:0.5 mole per liter of the alkali metal silicate is admixed with the aqueous medium, and the alkali metal silicate has an alkali metal oxide to silicon dioxide ratio between about 0.9:1.0 and 1.2:1.0.

30. The method of claim 19 wherein in the process of preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion, the aqueous medium contains about equimolar amounts of calcium ion and magnesium ion, about 0.2–0.3 mole per liter of the alkali metal silicate is admixed with the aqueous medium, and the alkali metal silicate is alkali metal metasilicate having an alkali metal oxide to silicon dioxide ratio of about 1.0:1.0.

31. The method of claim 30 wherein in the process for preparing the catalyst, the alkali metal metasilicate is sodium metasilicate having a sodium oxide to silicon dioxide ratio of about 1.0:1.0.

32. The method of claim 30 wherein in the process for preparing the catalyst, about 0.01–0.1 mole per liter of the surfactant is admixed with the aqueous medium.

33. The method of claim 32 wherein in the process for preparing the catalyst, the surfactant comprises sulfated castor oil.

34. The method of claim 33 wherein in the process for preparing the catalyst, the alkali metal metasilicate is sodium metasilicate having a sodium oxide to silicon dioxide ratio of about 1.0:1.0.

35. The method of claim 34 wherein in the process for preparing the catalyst, at least 50% of the hydroxy groups of the castor oil are sulfated, and about 0.03–0.07 mole per liter of the sulfated castor oil is admixed with the aqueous medium.

36. The method of claim 30 wherein in the process for preparing the catalyst, the alkali metal silicate is admixed with an aqueous medium containing said dissolved substances in amounts to provide about $2.9 \times 10^{-3}$ mole per liter of calcium ion and about $2.7 \times 10^{-3}$ mole per liter of magnesium ion, about 0.25 mole per liter of sodium metasilicate having a sodium oxide to silicon dioxide ratio of about 1.0:1.0 is admixed with the aqueous medium, the aqueous medium contains not more than 10 parts per million by weight of carbonate ion and bicarbonate ion, the surfactant comprises sulfated castor oil and at least 50% of the hydroxy groups of the castor oil as sulfated, and about 0.05 mole per liter of the sulfated castor oil is admixed with the aqueous medium.

37. A method of treating infected and damaged tissue and relieving stress and shock in warm blooded animals comprising administering thereto a therapeutically effective amount of a catalyst and a therapeutically effective amount of catalyst treated lignite, the said catalyst being prepared by a process comprising admixing a water soluble alkali metal silicate with an aqueous medium containing a dissolved substance which is a source of calcium ion and a dissolved substance which is a source of magnesium ion;

the aqueous medium containing said dissolved substances in amounts to provide between about $1 \times 10^{-4}$ and $1 \times 10^{-1}$ mole per liter each of calcium ion and magnesium ion, the aqueous medium containing said dissolved substances in amounts to provide a molar ratio of calcium ion to magnesium ion between about 2.0:1.0 and 1.0:2.0, the alkali metal silicate having an alkali metal oxide to silicon dioxide ratio between about 0.9:1.0 and less than 2.0:1.0 and being admixed with the aqueous medium in an amount of about 0.05–2 mole per liter.

reacting the alkali metal silicate with said dissolved substances providing calcium ion and magnesium ion to produce an aqueous suspension of finely divided particles of the reaction product, admixing a micelle-forming surfactant with the aqueous medium in an amount to form catalyst micelles comprising said finely divided particles of the reaction product upon agitating the aqueous medium, and agitating the aqueous medium containing the finely divided particles of the reaction product and surfactant to form said catalyst micelles; and the said catalyst treated lignite being prepared by a process comprising intimately contacting solid lignite in particulate form with a liquid aqueous medium containing a catalytically effective amount of the said catalyst, the said particles of the lignite having active sites therein which react with at least one component of the said aqueous medium containing the catalytically effective amount of the catalyst under liquid phase conditions and in the presence of the said catalyst, and the said the said particles of the liqnite being intimately contacted under liquid phase conditions until the active sites thereof react with at least one component of the said aqueous medium containing the catalytically effective amount of the catalyst and until the lignite is soluble in an aqueous medium.

38. The method of claim 37 wherein in the process for preparing the catalyst, said ratio of calcium ion to magnesium ion is between about 1.5:1.0 and 1.0:1.5.

39. The method of claim 37 wherein in the process for preparing the catalyst, said ratio of calcium ion to magnesium ion is about 1.0:1.0.

40. The method of claim 37 wherein in the process for preparing the catalyst, the alkali metal silicate is admixed with an aqueous medium containing said dissolved substance in amounts to provide between about $1 \times 10^{-3}$ and $6 \times 10^{-3}$ mole per liter each of calcium ion and magnesium ion.

41. The method of claim 37 wherein in the process for preparing the catalyst, the alkali metal silicate is admixed with an aqueous medium containing said dissolved substances in amount to provide between about $2.5 \times 10^{-3}$ and $3.0 \times 10^{-3}$ mole per liter each of calcium ion and magnesium ion.

42. The method of claim 37 wherein in the process for preparing the catalyst, about 0.2–0.5 mole per liter of the alkali metal silicate is admixed with the aqueous medium.

43. The method of claim 37 wherein in the process for preparing the catalyst, the alkali metal silcate has an alkali metal oxide to silicon dioxide ratio between about 0.9:1.0 and 1.2:1.0.

44. The method of claim 37 wherein in the process for preparing the catalyst, the alkali metal silicate is alkali metal metasilicate having an alkali metal oxide to silicon dioxide ratio of about 1.0:1.0.

45. The method of claim 37 wherein in the process for preparing the catalyst, about 0.01–0.1 mole per liter of the surfactant is admixed with the aqueous medium.

46. The method of claim 37 wherein in the process for preparing the catalyst, the surfactant comprises sulfated castor oil.

47. The method of claim 37 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion, the ratio of calcium ion to magnesium ion is between about 1.5:1.0 and 1.0:1.5, about 0.2:0.5 mole per liter of the alkali metal silicate is admixed with the aqueous medium, and the alkali metal silicate has an alkali metal oxide to silicon dioxide ratio between about 0.9:1.0 and 1.2:1.0.

48. The method of claim 37 wherein in the process for preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion, the aqueous medium contains about equimolar amounts of calcium ion and magnesium ion, about 0.2–0.3 mole per liter of the alkali metal silicate is admixed with the aqueous medium, and the alkali metal silicate is alkali metal metasilicate having an alkali metal oxide to silicon dioxide ratio of about 1.0:1.0.

49. The method of claim 48 wherein in the process for preparing the catalyst, the alkali metal metasilicate is sodium metasilicate having a sodium oxide to silicon dioxide ratio of about 1.0:1.0.

50. The method of claim 48 wherein in the process for preparing the catalyst, about 0.01–0.1 mole per liter of the surfactant is admixed with the aqueous medium.

51. The method of claim 50 wherein in the process for preparing the catalyst, the surfactant comprises sulfated castor oil.

52. The method of claim 51 wherein in the process for preparing the catalyst, the alkali metal metasilicate is sodium metasilicate having a sodium oxide to silicon dioxide ratio of about 1.0:1.0.

53. The method of claim 52 wherein in the process for preparing the catalyst, at least 50% of the hydroxy groups of the castor oil are sulfated, and about 0.03–0.07 mole per liter of the sulfated castor oil is admixed with the aqueous medium.

54. The method of claim 48 wherein in the process for preparing the catalyst, the alkali metal silicate is admixed with an aqueous medium containing said dissolved substances in amounts to provide about $2.9 \times 10^{-3}$ mole per liter of calcium ion and about $2.7 \times 10^{-3}$ mole per liter of magnesium ion, about 0.25 mole per liter of sodium metasilicate having a sodium oxide to silicon dioxide ratio of about 1.0:1.0 is admixed with the aqueous medium, the aqueous medium contains not more than 10 part per million by weight of carbonate ion and bicarbonate ion, the surfactant comprises sulfated castor oil and at least 50% of the hydroxy groups of the castor oil are sulfated, and about 0.05 mole per liter of the sulfated castor oil is admixed with the aqueous medium.

* * * * *